United States Patent [19]
Foster et al.

[11] Patent Number: 6,007,805
[45] Date of Patent: *Dec. 28, 1999

[54] USE OF INTERFERON SUBTYPE ALPHA-8 (IFN-α₈) TO TREAT VIRAL INFECTIONS OF THE LIVER

[75] Inventors: Graham Russell Foster; Howard Christopher Thomas, both of London, United Kingdom

[73] Assignee: Imperial College of Science and Technology, London, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/704,784

[22] PCT Filed: Mar. 7, 1995

[86] PCT No.: PCT/GB95/00488

§ 371 Date: Sep. 24, 1996

§ 102(e) Date: Sep. 24, 1996

[87] PCT Pub. No.: WO95/24212

PCT Pub. Date: Sep. 14, 1995

[30] Foreign Application Priority Data

Mar. 7, 1994 [GB] United Kingdom .................. 9404379
Oct. 10, 1994 [GB] United Kingdom .................. 9420340

[51] Int. Cl.⁶ .................................................. A61K 38/21
[52] U.S. Cl. .......................................... 424/85.7; 424/85.4
[58] Field of Search .................. 424/85.4, 85.7; 514/2

[56] References Cited

U.S. PATENT DOCUMENTS

5,503,828  4/1996  Testa et al. ............................ 424/85.7
5,676,942  10/1997 Testa et al. ............................ 424/85.7

FOREIGN PATENT DOCUMENTS

00438980  1/1982  European Pat. Off. .
WOP84/03105  8/1984  WIPO .
WO93/16107  8/1993  WIPO .

OTHER PUBLICATIONS

Lane, H. C., et al. (1990) *Am. Int. Med.* 112: 805–11.
Merimsky, O., et al. (1990) *Mol. Biother.* 2: 155–59.
Cantell K, et al 1995, Annals Med 27, 23, Feb. 1995.
Streuli, M et al 1981, PNAS 78,2848, May 5, 1981.
Bundesverband Der Pharmazeutische Industrie BV. "Rote Liste 1993" 1993, Editio Cantor, Aulendorf DE p. 50.
Antiviral Research, vol. 22, No. 2–3, 1993 Amsterdam, pp. 121–129, Sperber, S.J. et al, "Antirhinoviral activity of recombinant and hybrid species of interferon alpha".
Clinical Science, vo. 88, No. 2, Feb. 1995 Glasgow UK, p. 13;, Foster GR et al "Induction of, and response to, different interferon alpha subtypes in human cell lines".
Virology, vol. 130, 1983 New York, pp. 273–280, Tamar Goren et al "High and low petency interferon–alpha subtypes induce (2'–5') oligoadenylate synthetase with similar efficiency".
Journal of Interferon Research, vol. special issue, Jan. 1991 Chicago, pp. 185–194, Finter N.B., "Why are there so many subtypes of Alpha–interferons?".
Journal of Interferon Research, vol. 9, 1989 Chicago, pp. 97–114, Fish E.N. et al "The role of three domains in the biological activity of human Interferon–alpha".
Reynoldds, J.E.F., "Martindale, The extra Pharmacopoeia" 1989, The Pharmaceutical Press, London pp. 696–699.
Fan et al Aids Research and Human Retroviruses vol. 9, No. 11, 1993, pp. 1115–1122 Increased Efficacy of Human Natural Interferon α(IFN–αn3) etc.

*Primary Examiner*—David L. Fitzgerald
*Attorney, Agent, or Firm*—Nixon & Vanderhye

[57] ABSTRACT

Individual subtypes of interferon-α (IFN-α) have been found to have different antiviral activity in different cell types and are therefore used to prevent or treat viral infections in cell types in which they are most active. The individual subtype of choice has relatively low antiviral activity in other celltypes to reduce the risk of side effects. IFN-α₁₀ and/or IFN-α₁₇ are preferred for use in treating viral lung infections and IFN-α₈ is preferred for use in treating viral liver infections.

2 Claims, 1 Drawing Sheet

USE OF INTERFERON SUBTYPE ALPHA-8 (IFN-$\alpha_8$) TO TREAT VIRAL INFECTIONS OF THE LIVER This invention relates to the treatment or prophylaxis of viral infections with interferons (IFNs).

Type I interferons (IFN) are a family of closely related glycoproteins containing many IFN-$\alpha$ subtypes and one IFN-$\beta$ subspecies. At least 23 different human IFN-$\alpha$ subtypes have been identified by analysis of human CDNA libraries and by protein analysis of the IFNs produced by stimulated lymphoblastoid cells. The reasons for this heterogeneity are not yet known. Previous studies have suggested that all Type I IFNs bind to an identical receptor and therefore have identical effects. However a mutant cell line that responds only to IFN-$\beta$ but not IFN-$\alpha$ has been identified showing that these two IFN subspecies bind to a different receptor and may therefore have different effects. Studies on the recently identified transmembrane human IFN receptor have shown that if this receptor is transfected into murine cells the cells respond only to some IFN subtypes, showing that a second receptor component is required to allow cells to respond to IFN and that the murine equivalent of this component is able to distinguish between different IFN subtypes. Molecular analysis of the human Type I IFN receptor thus suggests that the receptor may be able to distinguish between different IFN subtypes, but whether the different subtypes do, in fact, have different effects is not yet clear. A number of studies have compared the effects of different IFN-$\alpha$ subtypes on the antiviral activities of human cell lines. Zoon et al (J. Biol. Chem. 267: 15210–16 (1992) studied IFNs that were obtained from HPLC purification of natural IFN and found no gross differences in their antiviral activities. However, Sperber et al, *J. Interferon. Res.* 12 363–368 (1992) examined the effects of different recombinant IFN-$\alpha$ subtypes on cells infected with the human immunodeficiency virus (HIV) and found marked differences in their antiviral properties.

Whereas the investigations of Sperber et al were confined to the effect of different subtypes of IFN-$\alpha$ against a particular virus (HIV-1), it has now been found that the antiviral effect of subtypes of IFN-$\alpha$ is dependent on the type of cell infected with the virus. Further, it appears that certain subtypes of IFN-$\alpha$ act as partial agonists to antivirally effective IFNs-$\alpha$. Therefore, by virtue of the invention, the use of specific subtypes of IFN-$\alpha$ for the treatment of each cell type is indicated.

DESCRIPTION OF THE INVENTION

Figure 1A:
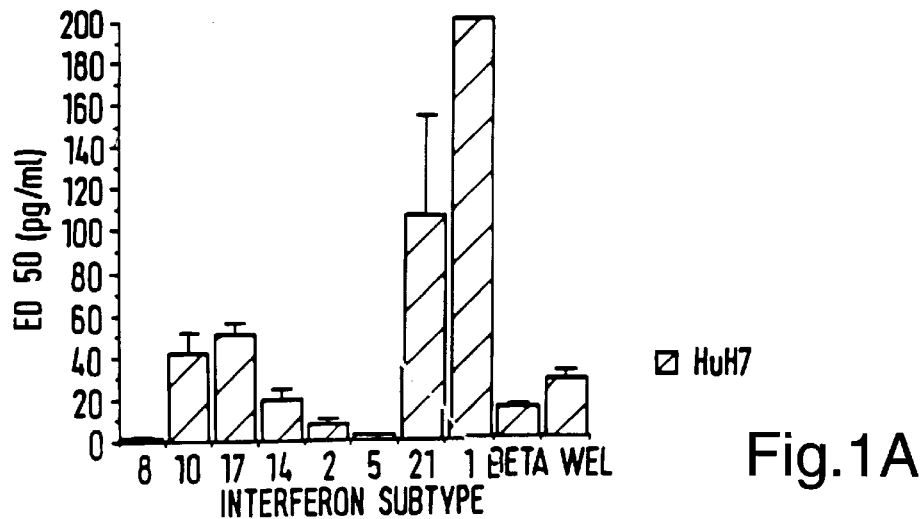
FIG. 1A is a graph showing the relative ED50 for various interferon subtypes in HuH7 cells.

According to the invention, there is provided the use of a single interferon-$\alpha$ (IFN-$\alpha$) subtype in the preparation of a medicament for preventing or treating viral infections of a particular organ or cell type.

The cell type will generally not be T-lymphocytes, in view of the prior work of Sperber et al. However, nothing in the Sperber et al publication referred to above suggests that IFNs-$\alpha$ exhibit cell-type specific antiviral activity.

A particularly preferred IFN-$\alpha$ subtype is IFN-$\alpha_8$. This is particularly suitable for treating or preventing viral infections of the liver. In addition to its potent antiviral effects in normal cell lines, IFN-$\alpha_8$ is also active in a mutant cell line (11,1 (Pellegrini et al, *Mol. Cell. Biol.* 9: 4605–4612 (1989))) that does not respond to other $\alpha$ IFN subtypes.

The particular IFN-$\alpha$ subtype to be used in clinical practice will depend on the cell type which is infected. Preferred subtypes for a particular cell type may be those which not only have potent antiviral activity for that particular cell type but also have relatively low activity in respect of other cell types, so as to reduce the possibility of side effects.

For example, when choosing an IFN-$\alpha$ subtype for use in lung infections, regard will be had to in vitro studies on lung carcinoma cell lines which showed that IFN-$\alpha_2$, IFN-$\alpha_5$, IFN-$\alpha_8$, IFN-$\alpha_{14}$ and IFN-$\alpha_{17}$ were the most potent subtypes tested and IFN-$\alpha_{10}$ had high activity. However, IFN-$\alpha_2$, IFN-$\alpha_5$, IFN-$\alpha_8$ and IFN-$\alpha_{14}$ were also very potent antivirals in liver cell lines. Thus, it may be the case that the preferred subtypes for treating or preventing viral infections of the lung are IFN-$\alpha_{10}$ and IFN-$\alpha_{17}$.

When choosing an IFN-$\alpha$ subtype for use in liver infections, regard will also be had to in vitro studies on liver cell lines which showed that IFN-$\alpha_2$, IFN-$\alpha_5$ and IFN-$\alpha_8$ were the most potent subtypes tested. IFN-$\alpha_2$ and IFN-$\alpha_5$ were, as mentioned above, also potent antivirals in a liver cell line. However, although this is also true of IFN-$\alpha_8$, it has also been observed that, in vitro, cells appear to produce IFN-$\alpha_8$, in response to viral infection. Thus, the preferred subtype for treating or preventing viral infections of the liver is IFN-$\alpha_8$.

Mixtures of a small number (such as two, three or four) specific IFNs-$\alpha$ are also contemplated within the scope of the invention. Each will generally be selected in accordance with the guidelines given above.

IFN-$\alpha$ subtypes may be administered by conventional means and at doses comparable to those known in the art, although the precise mode of administration and dosage will always be within the discretion of the physician or other medical practitioner.

The invention has application in a method of preventing or treating viral infections of a particular organ or cell type, the method comprising administering an effective antiviral amount of a single interferon-$\alpha$ (IFN-$\alpha$) subtype.

The invention will now be illustrated by the following example.

EXAMPLE a) Interferons

WELLFERON™ lymphoblastoid interferons were obtained from The Wellcome Foundation Limited. Human Type I interferons were prepared by stimulating Namalwa cells with Sendai virus and then purifying and fractionating the IFN mixture using antibody precipitation and HPLC purification, as previously described (Zoon et al, *J. Biol. Chem.* 267: 15210–15216 (1992)). IFNs were also prepared, in a similar manner, from supernatants of Sendai virus-treated human peripheral blood mononuclear cells (Interferon Sciences Inc). The identity of the purified IFN subtype fractions was confirmed by microsequencing a fraction of the column eluate and the concentration of the final product was determined using a commercial kit (Sigma).

b) Antiviral assays

Human cell lines (HuH7, A549 and SHSY) were grown in DMEM supplemented with 10% FCS. Antiviral assays were performed as described (Zoon et al, supra). In brief, cells were transferred to 96 well microtitre plates ($1.5-2\times10^4$ cells per well) and grown in the presence of IFN for 23 hours. The IFN-containing medium was removed and cells were incubated with virus (EMC virus or HAV) for 1 hour. After removing the virus, the cells were left for 24 hrs and viable cells stained with methyl violet. The number of viable cells was determined by measuring the optical density of each well. Duplicates of six five fold dilutions of IFN were included in each assay and each assay was repeated at least four times. Antiviral activity of each subtype was compared to lymphoblastoid IFN (WELLFERON™) of known activity ($10^8$ IU/ml)

Results a) Antiviral Activity

Figure 1B:
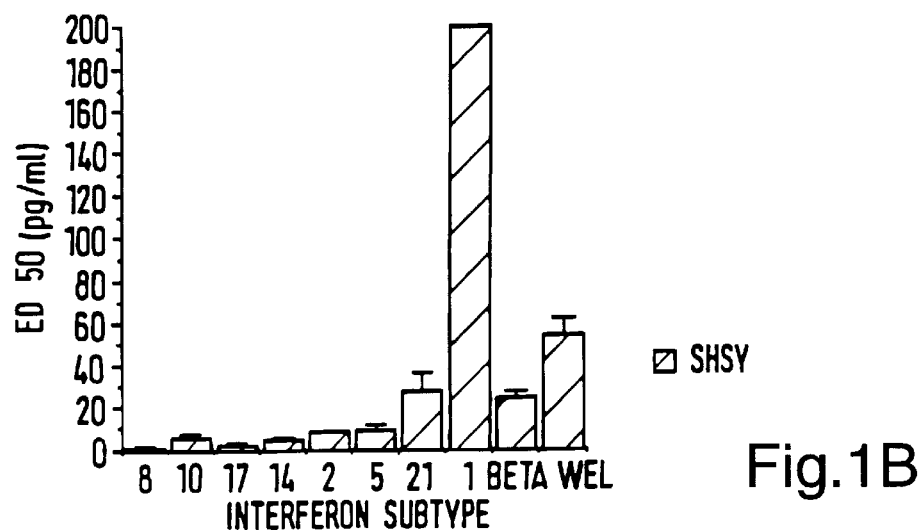
FIG. 1B is a graph showing the relative ED50 for various interferon subtypes in SHSY cells.
Figure 1C:
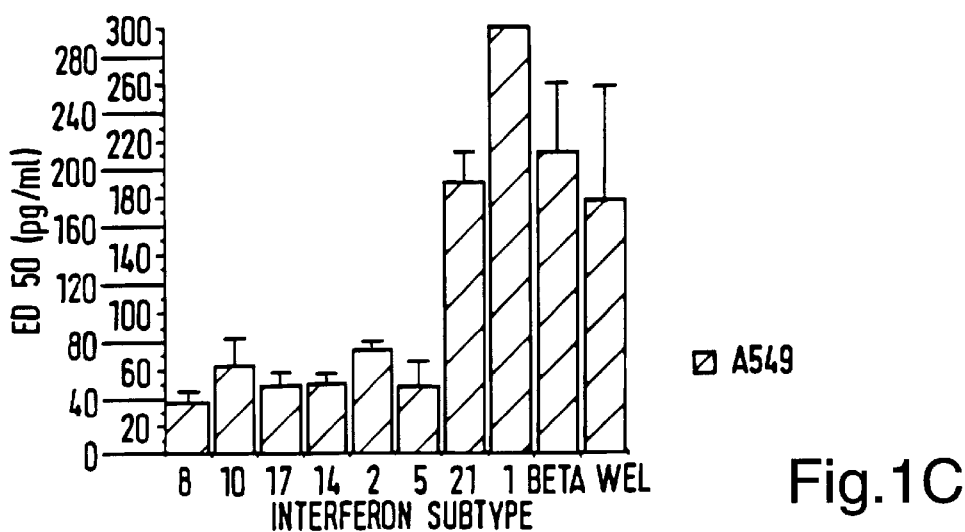
FIG. 1C is a graph showing the relative ED50 for various interferon subtypes in A549 cells.

The antiviral effects of some of the different IFN subtypes in HuH7 (liver), A549 (lung) and SHSY (neuroblastoma) cells challenged with EMC virus are shown in FIGS. 1A, 1B and 1C which give the ED50 (dose of IFN causing 50% inhibition of viral replication) for all different subtypes.

The efficacy of the different subtypes was similar in another liver cell line (HepG2) (data rot shown) and a similar trend was seen when HuH7 cells were challenged with another virus (hepatitis A virus). There was a marked difference in the relative efficacies of the different subtypes between the cell lines: in liver cell lines IFN-$\alpha_8$, -$\alpha_8$ and -$\alpha_2$ were very potent whilst IFN-$\alpha_{17}$, had relatively little antiviral activity. In lung carcinoma cell lines IFN-$\alpha_8$, -$\alpha_{17}$, -$\alpha_{10}$, -$\alpha_5$ and -$\alpha_{14}$ were the most potent subtypes tested. IFN-$\alpha_1$ had very poor activity.

When the anti-viral effects of the different subtypes were analysed using the interferon resistant cell line 11,1, only IFN-$\alpha_8$ inhibited the cytopathic effects, indicating that this type of subtype has unique properties not shared by the other IFN-$\alpha$ subtypes.

Discussion

1. Between cell lines there are differences in antiviral activity between different subtypes; therefore it may be necessary to use specific subtypes for treatment of infection of each cell type in clinical practice: infections of liver and lung may require different IFN subtypes.

2. IFN-$\alpha_2$, IFN-$\alpha_8$ and -$\alpha_5$ are active against both liver and lung cell lines; therefore they may induce most side effects in patients—should use a cell specific subtype to reduce side effects—(eg $\alpha_8$ for hepatocytes).

3. However, in view of cells' response to viral infection, i.e production of IFN-$\alpha_8$, this subtype may be the subtype of choice generally.

4. In view of the specific activity of IFN-$\alpha_8$ in mutated cell lines, this subtype may have additional desirable properties and may be effective when other subtypes are inactive.

We claim:

1. A method of treating a patient having a viral infection predominantly localized in the liver, the method comprising administering to said patient a composition consisting essentially of an effective antiviral amount of interferon $\alpha_8$(IFN-$\alpha_8$).

2. The method of claim 1, wherein the viral infection is a hepatitis viral infection.

* * * * *